(12) United States Patent
Boger et al.

(10) Patent No.: US 11,963,945 B2
(45) Date of Patent: *Apr. 23, 2024

(54) OZONIDES FOR TREATING OR PREVENTING VIRUS INFECTIONS

(71) Applicants: THE JOHNS HOPKINS UNIVERSITY, Baltimore, MD (US); Board of Regents of the University of Nebraska, Omaha, NE (US)

(72) Inventors: Ravit Boger, Baltimore, MD (US); Jonathan Vennerstrom, Omaha, NE (US)

(73) Assignees: THE JOHNS HOPKINS UNIVERSITY, Baltimore, MD (US); BOARD OF REGENTS OF THE UNIVERSITY OF NEBRASKA, Omaha, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/570,376

(22) Filed: Jan. 6, 2022

(65) Prior Publication Data

US 2022/0202769 A1 Jun. 30, 2022

Related U.S. Application Data

(63) Continuation of application No. 16/613,258, filed as application No. PCT/US2018/032632 on May 15, 2018, now Pat. No. 11,246,854.

(60) Provisional application No. 62/506,757, filed on May 16, 2017.

(51) Int. Cl.
A61K 31/357 (2006.01)
A61K 31/4525 (2006.01)
A61K 31/5377 (2006.01)
A61P 31/22 (2006.01)

(52) U.S. Cl.
CPC ........ *A61K 31/357* (2013.01); *A61K 31/4525* (2013.01); *A61K 31/5377* (2013.01); *A61P 31/22* (2018.01)

(58) Field of Classification Search
CPC ............ A61K 31/5377; A61K 31/4525; A61K 31/357; A61P 31/22
See application file for complete search history.

(56) References Cited

U.S. PATENT DOCUMENTS

| 5,086,076 A | 2/1992 | Herman |
| 5,190,979 A | 3/1993 | Herman |
| 5,465,879 A * | 11/1995 | La .................. B05C 11/1034 222/525 |

FOREIGN PATENT DOCUMENTS

EP 2203457 B1 * 3/2014 .............. A61P 33/00

OTHER PUBLICATIONS

Barger-Kamate et al.("Effect of Artemether-Lumefantrine (coartem) on cytomegalovirus urine viral load and following treatment for Malaria in children," J. Clinc. Virology, 2016, vol. 77, pp. 40-45 (Year: 2016).*
Biron "antiviral drugs for cytomegalovirus diseases," Antiviral Research, 2006, vol. 71, pp. 154-163 (Year: 2006).*

(Continued)

*Primary Examiner* — Shengjun Wang
(74) *Attorney, Agent, or Firm* — Casimir Jones, S.C.; Kelly A. Barton

(57) ABSTRACT

Described are methods of treating or preventing a virus in a subject comprising administering ozonides to the subject.

16 Claims, 10 Drawing Sheets

A

(56) References Cited

OTHER PUBLICATIONS

Charman et al., "Synthetic ozonide drug candidate OZ439 offers new hope for a single-dose cure of uncomplicated malaria" Proc Natl Acad Sci U S A. Mar. 15, 2011;108(11):4400-5.
Dong, Y.; "Spiro and Dispiro-1,2,4-Trioxolanes as Antimalarial Peroxides: Charting a Workable SAR Using Simple Prototypes." J. Med. Chem. 2005, 48: 4953-4961.
Effert et al., "The antiviral activities of artemisinin and artesunate" Clin Infect Dis. Sep. 15, 2008;47(6):804-11.
Lu et al., "Human cytomegalovirus infection inhibits cell cycle progression at multiple points, including the transition from G1 to S" J Virol. Dec. 1996;70(12):8850-7.
Mathiowitz et al., "Biologically erodable microspheres as potential oral drug delivery systems" Nature. Mar. 27, 1997;386(6623):410-4.
Roy et al., "Human Cytomegalovirus Inhibits the PARsylation Activity of Tankyrase—A Potential Strategy for Suppression of the Wnt Pathway" Viruses 2016, 8(8), 17 pages.
Sinclair, "Human cytomegalovirus mediates cell cycle progression through G(1) into early S phase in terminally differentiated cells" J Gen Virol. Jun. 2000; 81(Pt 6):1553-65.
Takenaga et al., "Microparticle resins as a potential nasal drug delivery system for insulin" J Control Release. Mar. 2, 1998;52(1-2):81-7.
Tang et al., "Synthetic Peroxides as Antimalarials." Med. Res. Rev. 2004, 24: 425-448.
Tilley et al., "Semisynthetic Artemisinin and Synthetic Peroxide Antimalarials." In Neglected Diseases and Drug Discovery; Palmer, M. J., Wells, T. N. C., Eds.; Royal Society of Chemistry: Cambridge, UK, 2012, pp. 33-64.
Vennerstrom et al., "Peroxides as Oxidant Antimalarials." Drug Design and Delivery 1989, 4: 45-54.
Xue et al., "Effect of ozonide OZ418 against Schistosoma japonicum harbored in mice" Parasitol Res. Sep. 2014; 113(9):3259-66.
Zhou et al., "Characterization of the Two Major CYP450 Metabolites of Ozonide (1,2,4-trioxolane) OZ277" Bioorg. Med. Chem. Lett. 2008, 18: 1555-1558.

\* cited by examiner

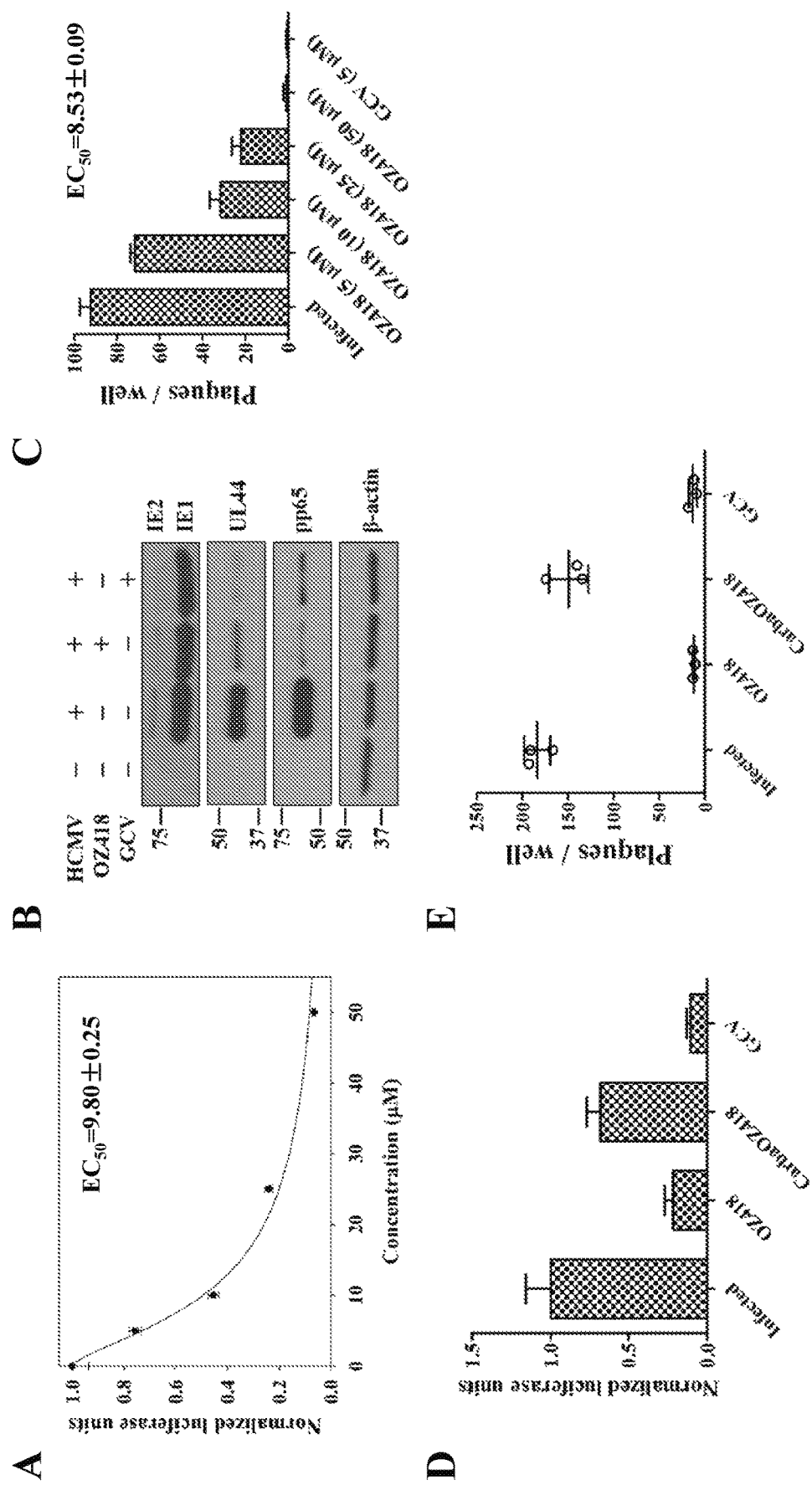
FIG. 2A-E

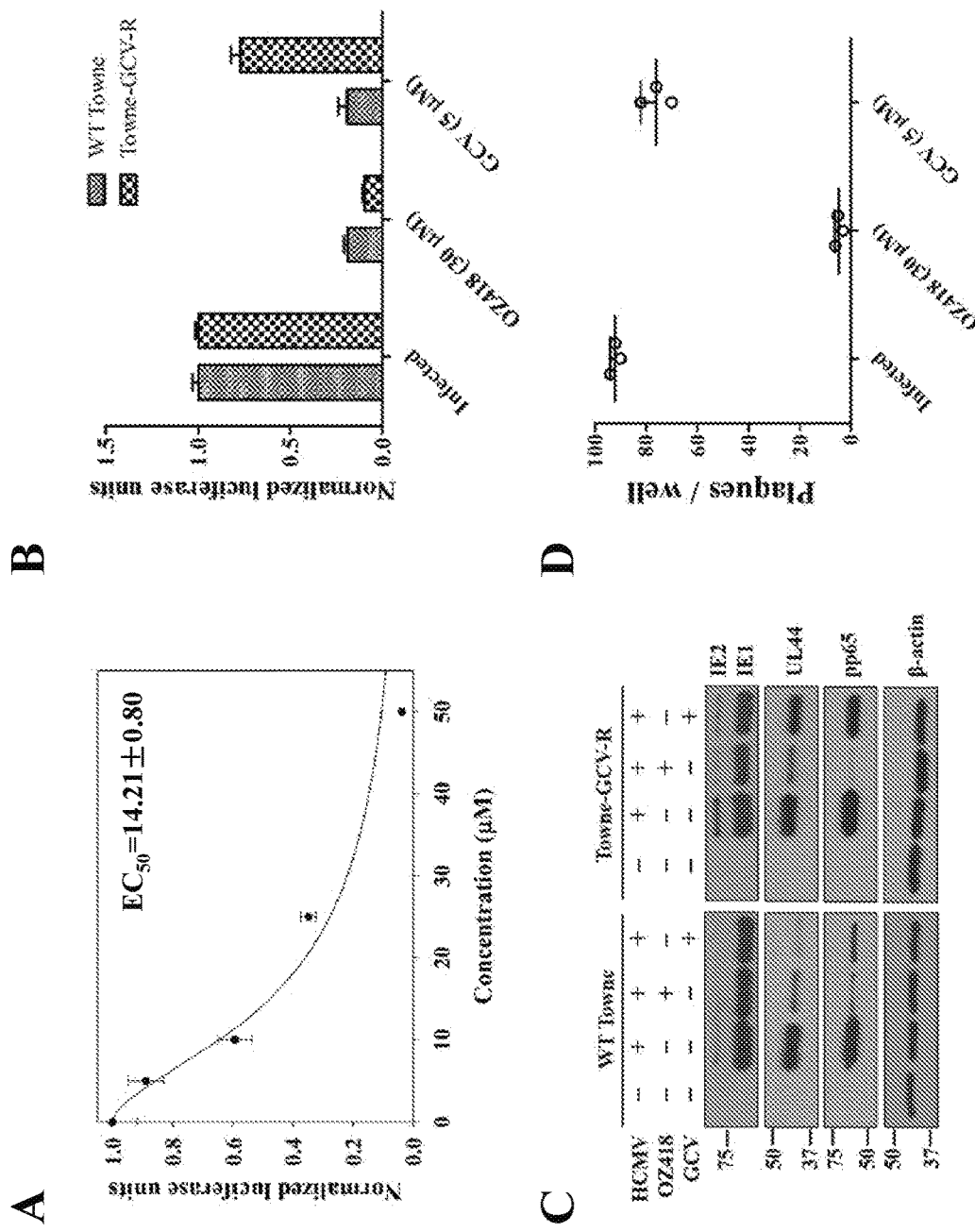
FIG. 3A-D

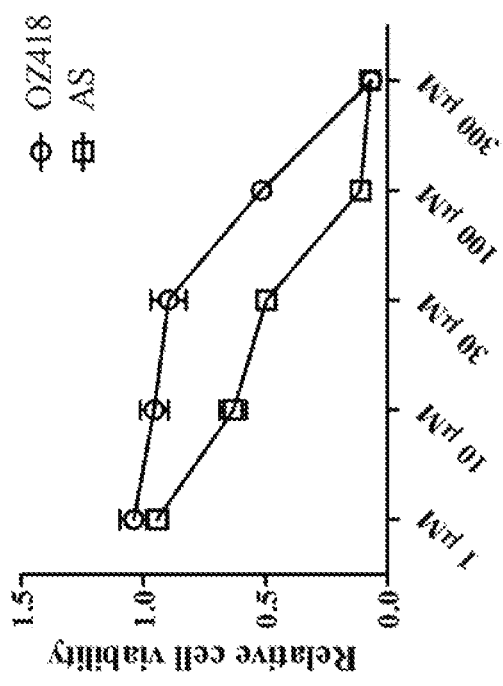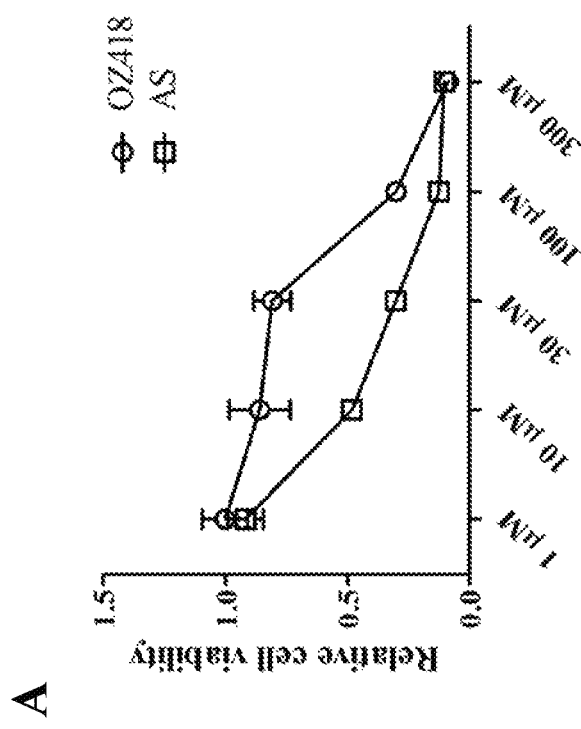
FIG. 9A-B

OZONIDES FOR TREATING OR PREVENTING VIRUS INFECTIONS

REFERENCE TO RELATED APPLICATIONS

This application claims the benefit of U.S. Provisional Patent application 62/506,757, filed May 16, 2017, which is hereby incorporated by reference for all purposes as if fully set forth herein.

STATEMENT OF GOVERNMENTAL INTEREST

This invention was made with government support under grants AI116723 and AI093701 awarded by the National Institutes of Health. The government has certain rights in the invention.

BACKGROUND OF THE INVENTION

Infection with human cytomegalovirus (HCMV), a member of the herpesvirus family, is common in humans. Seroprevalence rates increase with age, reaching 90% in individuals older than 80 years. While infection is typically asymptomatic HCMV continues to be a serious threat for transplant recipients and patients with AIDS. It is also the most common congenital infection worldwide causing hearing loss, mental retardation, and central nervous system damage in children.

The systemic anti-CMV drugs target the viral DNA polymerase and efficiently suppress virus replication. However, their use is associated with considerable toxicities to the bone marrow (ganciclovir [GCV]) and kidneys (foscamet and cidofovir), and emergence of resistant viruses. Until recently, intravenous GCV was the only approved drug for congenital CMV infection with central nervous system involvement, based on a phase III clinical trial that documented prevention of hearing loss in treated children. A phase III clinical trial of oral valganciclovir (the valyl-ester prodrug of GCV) in congenitally-infected infants suggests that 6 months' therapy may have a better neurological outcome than 6 weeks, but GCV-resistant mutants can emerge. Widespread use of a limited number of drugs often leads to the development of drug-resistant strains. Thus, new targets are needed for CMV therapy.

Artemisinins, drugs of choice for malaria, gained interest because of their anti-HCMV activities. Artesunate (AS) and artemether are orally available, well-tolerated and safe. Millions of children have been treated with artemisinins for malaria, with no significant adverse effects. These properties are important because prolonged therapy is required for HCMV disease. Not surprisingly, AS was already administered to several immunocompromised patients with HCMV disease and variable results were reported. These reports illustrate the need to consider the pharmacokinetics (PK) and tissue distribution of artemisinins for HCMV therapeutics. While the very short half-life of AS may not be a barrier for malaria therapy, since its peak level is the determinant for clearance of the malaria parasites, continuous HCMV suppression will most likely depend on the area under the curve (AUC).

SUMMARY OF THE INVENTION

Towards this goal, the inventors tested the anti-HCMV activity of ozonides (1,2,4-trioxolanes) with extended half-lives. These compounds are new category of bioactive peroxides, developed by simplification of the chemical structure of artemisinin. Ozonide OZ277 (arterolane) in combination with piperaquine (Synriam™) was approved in 2012 for the treatment of malaria patients in India, and ozonide OZ439 (artefenomel) is now in phase IIb clinical trials.

In accordance with an embodiment, the present invention provides a compound of formula I:

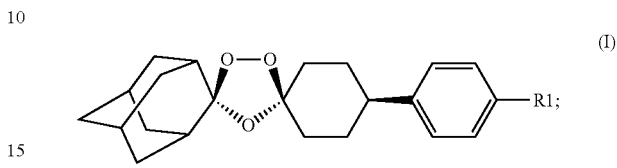

(I)

wherein R1 is selected from the group comprising alkyl, cycloalkyl, ether, carboxylic acid, weak base, or other polar functional groups or a pharmaceutically acceptable salt, solvate, or stereoisomer thereof.

Another embodiment of the present invention is a method of inhibiting virus replication comprising the following steps: providing a biological sample comprising a virus selected from the group comprising a herpesvirus that is replicating; applying a compound of Formula I to the sample;

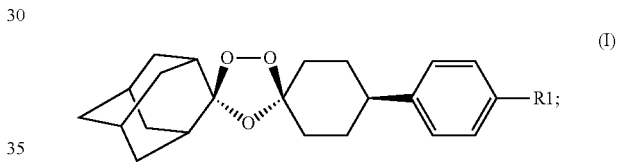

(I)

wherein R1 is selected from the group comprising alkyl, cycloalkyl, ether, carboxylic acid, weak base, or other polar functional groups or a pharmaceutically acceptable salt, solvate, or stereoisomer thereof; and inhibiting the replication of the virus. Examples of herpesvirus that may be used in the methods of the present invention include a cytomegalovirus (CMV), a varicella zoster (VZV), a herpesvirus 1 (HSV1), a herpesvirus 2 (HSV2), a human herpesvirus 6 (HHV6), a human herpesvirus 8 (HHV8) or a combination thereof. Examples of compounds of Formula I, salt, solvate, or stereosisomer thereof used in the methods of the present invention may be one of the following:

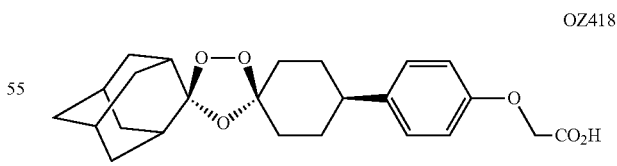

OZ418

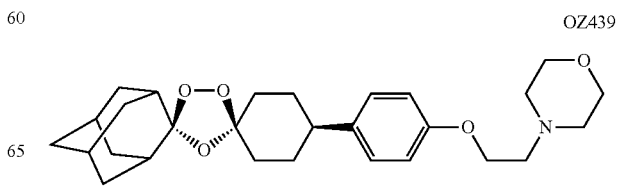

OZ439

-continued

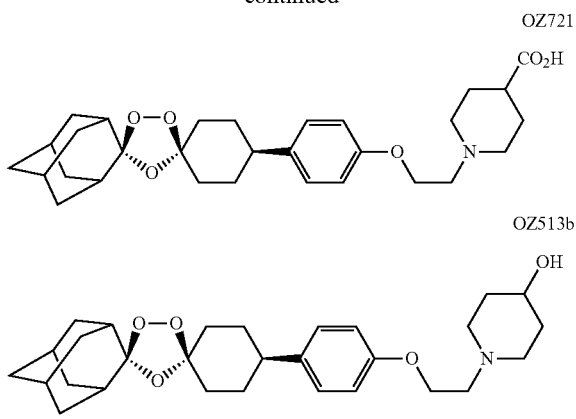

OZ721

OZ513b

Suitable biological samples used in the methods of the present invention include blood, cells, tissue, or a combination thereof, as examples, but any biological samples including virus may be used. The methods of the present invention may occur in vivo, such as in a subject having a virus infection, or in vitro, such as in cultured cells, as examples. Consequently, the methods of the present invention may inhibit the replication of the virus is in vitro or in vivo.

Another embodiment of the present invention is a method of treating or preventing a virus infection in a subject comprising: administering a compound of Formula I

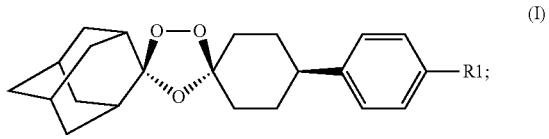

(I)

wherein R1 is selected from the group comprising alkyl, cycloalkyl, ether, carboxylic acid, weak base, or other polar functional groups or a pharmaceutically acceptable salt, solvate, or stereoisomer thereof; to a subject. A suitable subject may have a herpesvirus infection or is likely to obtain a herpesvirus infection. The administering of a compound of Formula I, or a combination of compounds of Formula I, treats or prevents a virus infection, including a herpesvirus infection, in the subject.

Another embodiment of the present invention is a pharmaceutical composition comprising one or more compounds described herein, including compound I, which may be administered during the methods of the present invention. Pharmaceutical compositions including one or more compounds of the present invention are administered to the subject by any suitable means based on the application. For example, a pharmaceutical composition of the present invention may be administered topically, orally or both, as examples.

By "agent" is meant any small molecule chemical compound.

By "ameliorate" is meant decrease, suppress, attenuate, diminish, arrest, or stabilize the development or progression of a disease.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels."

By "analog" is meant a molecule that is not identical, but has analogous functional or structural features.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "disease" is meant any condition or disorder that damages or interferes with the normal function of a cell, tissue, or organ. Examples of diseases include pancreatic cancer.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

As used herein, "obtaining" as in "obtaining an agent" includes synthesizing, purchasing, or otherwise acquiring the agent.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

By "reduces" is meant a negative alteration of at least 10%, 25%, 50%, 75%, or 100%.

By "reference" is meant a standard or control condition.

As used herein, the term "sensitivity" is the percentage of subjects with a particular disease.

As used herein, the term "specificity" is the percentage of subjects correctly identified as having a particular disease i.e., normal or healthy subjects. For example, the specificity is calculated as the number of subjects with a particular disease as compared to non-cancer subjects (e.g., normal healthy subjects).

As used herein, the term "subject" is intended to refer to any individual or patient to which the method described herein is performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 2A-2E illustrates in vitro anti-HCMV activity of OZ418. A. Dose response curve of OZ418 against the pp28-luciferase Towne CMV strain. B. Inhibition of HCMV viral protein expression. C. plaque reduction assay (TB40). D. 418 lacking the oxygen bridge has no anti-HCMV activity. E. Plaque reduction assays of OZ418 and deoxy 418.

FIG. 3A-3D illustrates activity of OZ418 against a GCV-resistant CMV strain. A. Dose response. B. Luciferase. C. HCMV proteins IE1/2, UL44, and pp65 detection. D. Plaque reduction assay.

FIG. 9A-9B illustrates cytotoxicity of OZ418 on HCT116 cells.

DETAILED DESCRIPTION OF THE INVENTION

Inhibition of HCMV Replication with Ozonides.

Figure 1:
FIG. 1 illustrates examples of chemical structures of ozonide analogs.

Six ozonizes have been tested for inhibition of HCMV replication and toxicity in human foreskin fibroblasts (Table 1, FIG. 1). The pp28 luciferase-recombinant Towne was used to measure HCMV replication, and an MTT assay—for cell viability. Of the 6 ozonides (OZ), OZ418 showed the best selectivity based on $CC_{50}/EC_{50}$. (FIG. 1). In a plaque reduction assay using the HCMV TB40 strain, the $EC_{50}$ of OZ418 was 8.53±0.09 µM. CarbaOZ418, the non-peroxide OZ418 could not inhibit HCMV as evidenced by pp28-luciferase activity and plaque reduction assay (FIGS. 2D and E).

| Compound | $EC_{50}$ (µM) | $CC_{50}$ (µM) | Selectivity index (SI) |
|---|---|---|---|
| OZ418 | 9.80 ± 0.25 | 128.10 ± 8.00 | 13.06 ± 0.48 |
| OZ439 | 13.19 ± 1.27 | 113.62 ± 13.22 | 8.62 ± 0.83 |
| OZ721 | 5.75 ± 0.74 | 45.49 ± 6.82 | 7.89 ± 0.35 |
| OZ513b | 15.74 ± 0.87 | 49.42 ± 3.67 | 3.14 ± 0.20 |
| NP20 | 20.27 ± 2.54 | 40.16 ± 1.47 | 2.00 ± 0.18 |
| OZ277 | 17.08 ± 1.31 | 33.69 ± 1.00 | 1.98 ± 0.09 |

Inhibition of GCV-Resistant HCMV with OZ418.

A GCV-resistant strain was inhibited by OZ418 (FIG. 3).

Timing of HCMV Inhibition by OZ418.

Figures 4A, 4B, 4C, 4D, 4E:
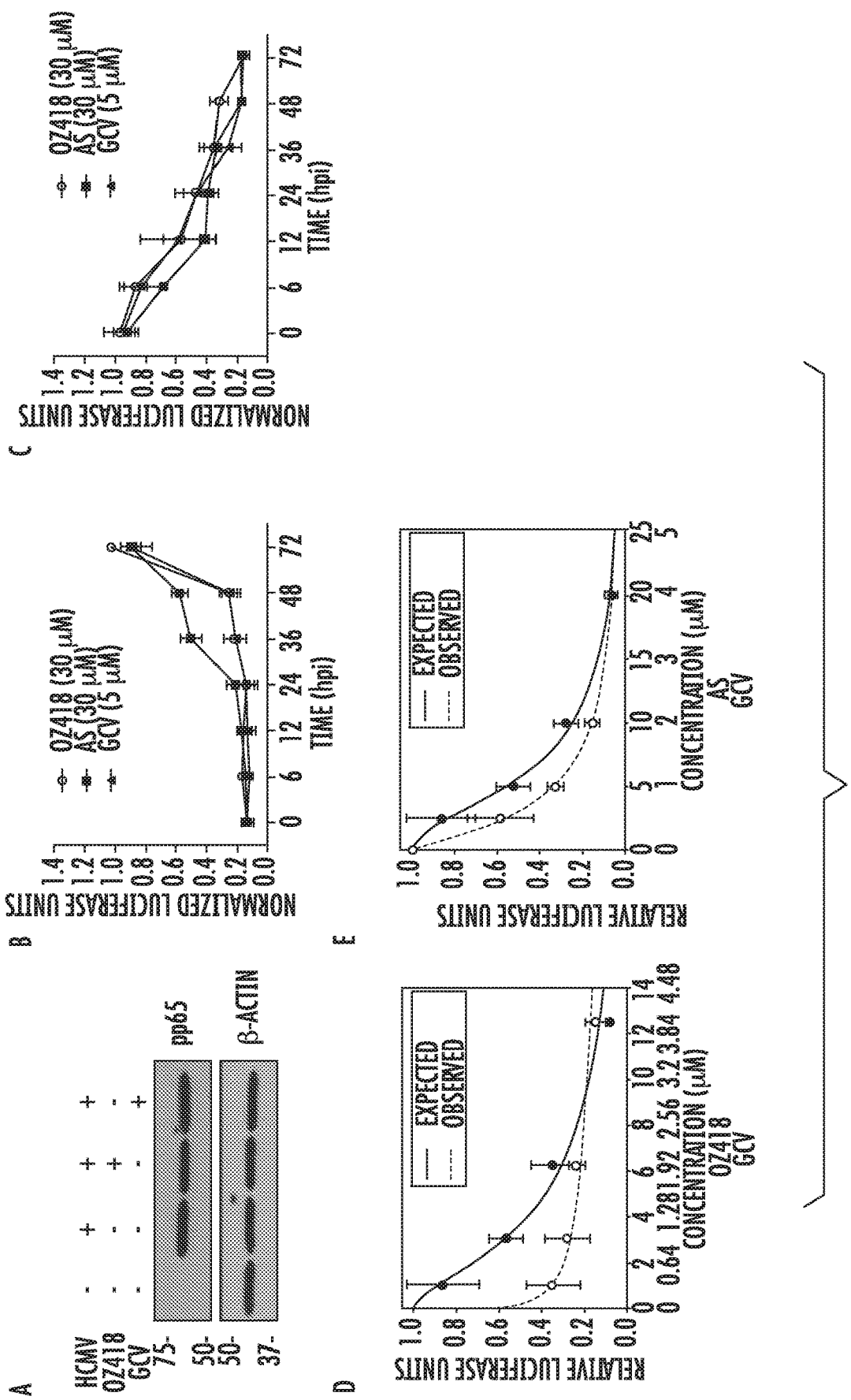
FIG. 4A-4E illustrates OZ418 is an early-late inhibitor of HCMV. A. Entry assays. B, C. Add-on and removal experiments. D, E. OZ418 is synergistic with GCV against HCMV.

To determine the time during HCMV replication that OZ418 was active an entry assay was performed (FIG. 4A). OZ418 did not inhibit HCMV entry. An add-on and removal assay showed that the timing of OZ418 activities was similar to GCV. In contrast, AS already lost anti-HCMV activity when added after 24 h post infection. Both AS and OZ418 showed synergistic activity with GCV against HCMV (FIGS. 4D and E). OZ418 effectively inhibits mouse CMV replication.

Figures 5A, 5B, 5C, 5D, 5E, 5F:
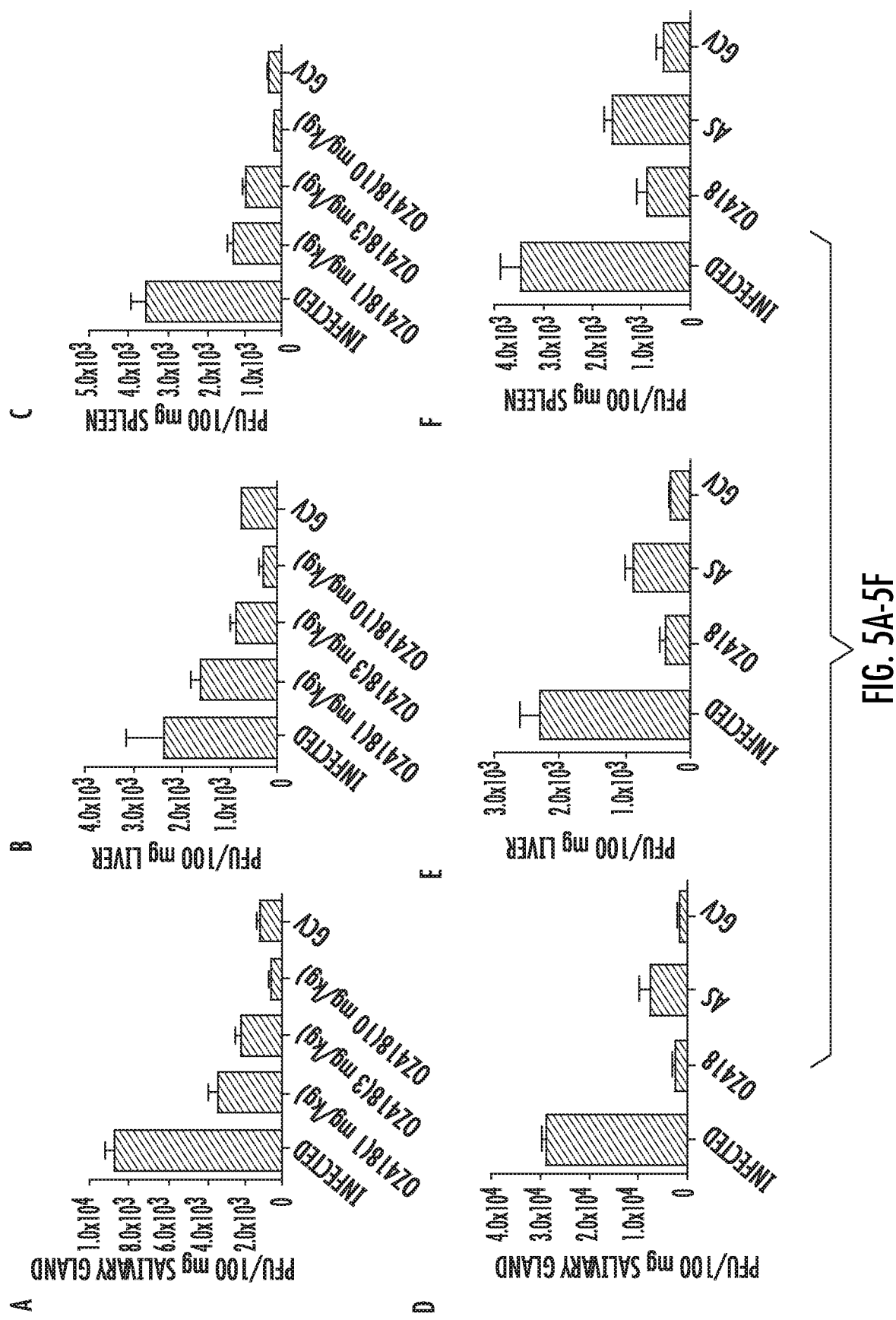
FIG. 5A-5F illustrates OZ418 efficiently inhibits MCMV replication. A, B, C. Dose response of OZ418. D, E, F. Comparison of AS (twice daily dosing) and OZ418 (once daily dosing).

The activity of OZ418 was tested in BALB/c mice infected with MCMV. A dose response was observed in salivary gland, liver and spleen at day 14 after infection. Compared to AS administered orally twice daily, OZ418 at once daily dosing was more effective in MCMV inhibition (FIG. 5D-F). Thus, OZ418 has improved efficacy against MCMV replication compared to AS.

Effect on OZ418 on Cell Cycle Progression in Non-Infected and HCMV-Infected HFFs.

AS was reported to arrest cell cycle in early G1. We therefore tested the effect of OZ418 on cell cycle progression. In non-infected cells OZ418 did not influence cell cycle progression (FIG. 6); cells did not arrest in G1. However, in HCMV-infected cells OZ418 delayed cell cycle progression (Shenk 1996, Sinclair 2000 (cell cycle) (34, 35). In these cells the expression level of CDK 1, 2, 4, pRb and E2F1 was reduced in infected cells treated with OZ418. HCMV infection induced the expression of CDK 1, 2 and 4 and the phosphorylation of pRb (Ser 807/811). In non-infected cells the expression of CDKs, pRB and E2F1 was unchanged with OZ418, suggesting the effects of OZ418 were induced in infected cells.

Figures 6A, 6B, 6C, 6D:
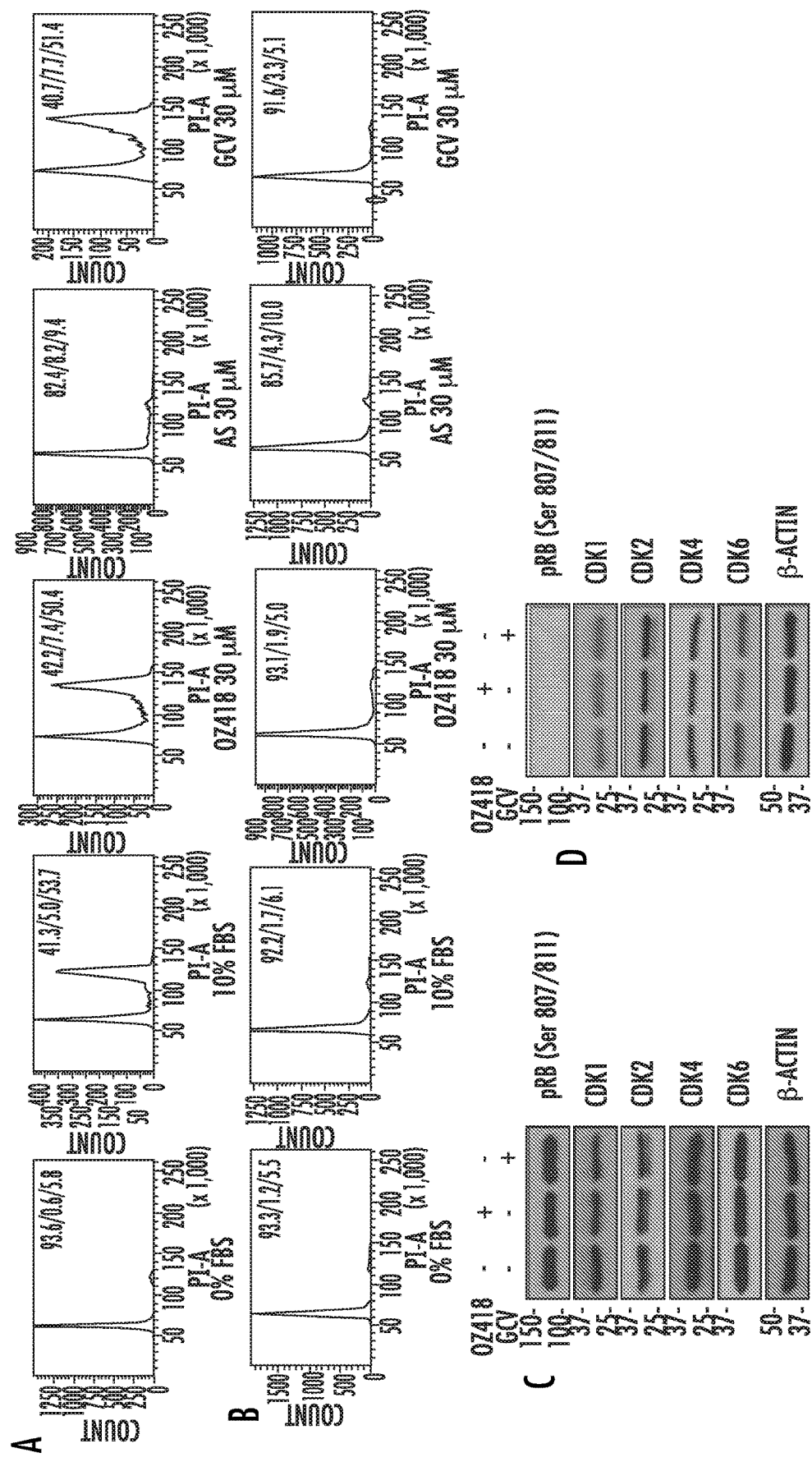
FIG. 6A-D illustrates OZ418 does not regulate cell cycle progression in non-infected HFFs. A. Flow data 24 h. B. Flow data 72 h. C. 24 h protein expression. D. 72 h protein expression.
Figures 7A, 7B, 7C, 7D:
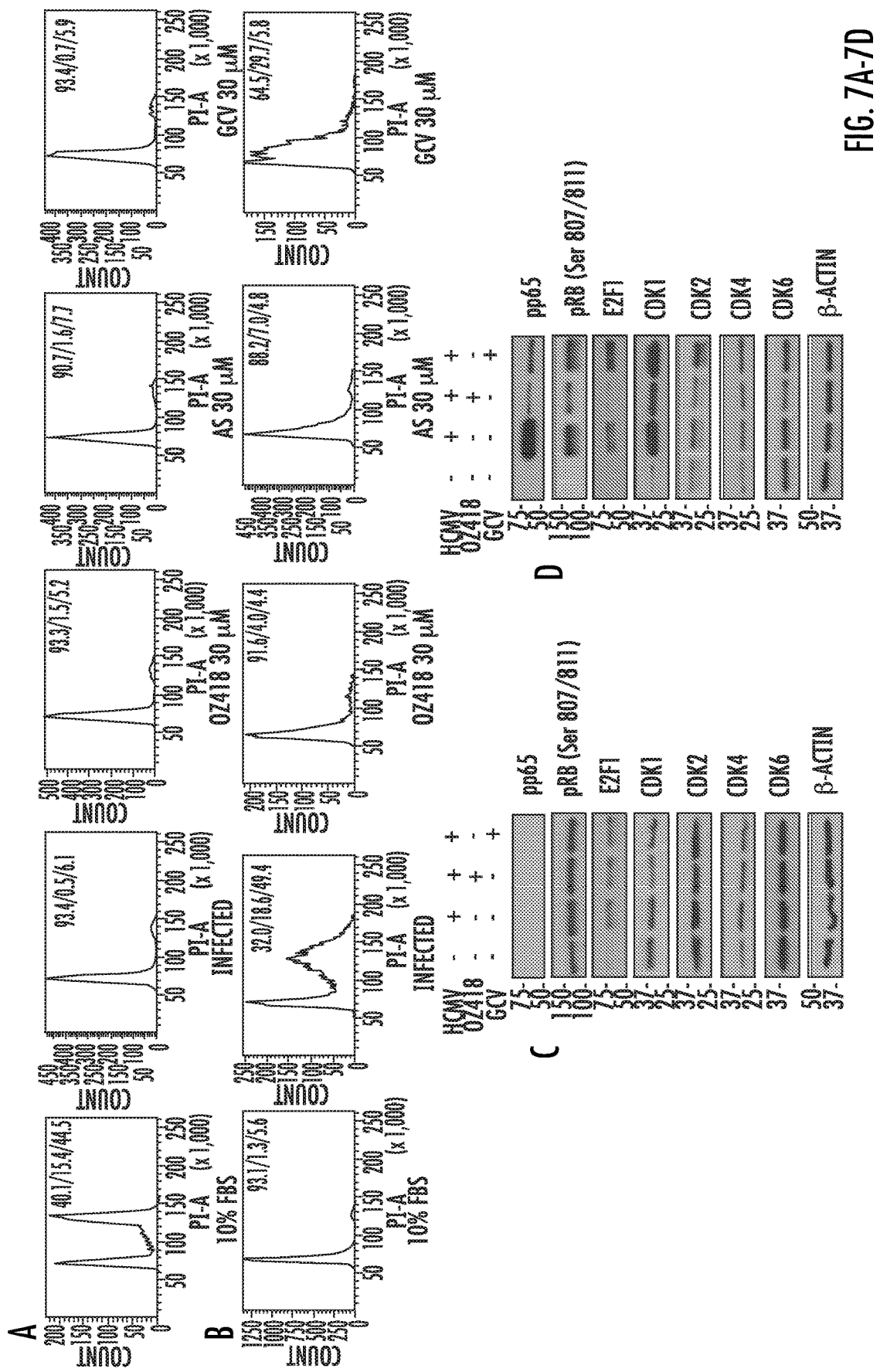
FIG. 7A-7D illustrates OZ418 regulates cell cycle progression in HCMV-infected HFFs. A. Flow data 24 h. B. Flow data 72 h. C. pRb and CDK expression detection 24 h. D. pRb and CDK expression detection 72 h.
Figure 8A:
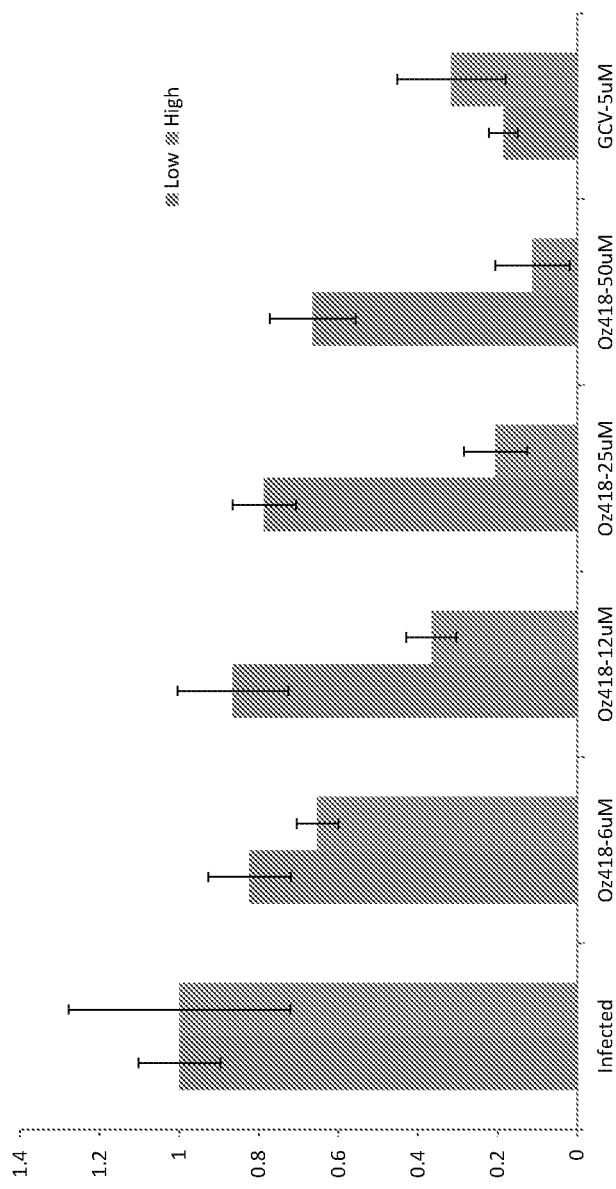
FIG. 8A-8B illustrates ozonide treatment. A. pp28 Luciferase activity in high density and low density HFFs infected with HCMV and treated with 418. B. Western blot of CDKs, pRb and E2F1 in high and low density HFFs infected with HCMV and treated with OZ418 or GCV.
Figure 8B:
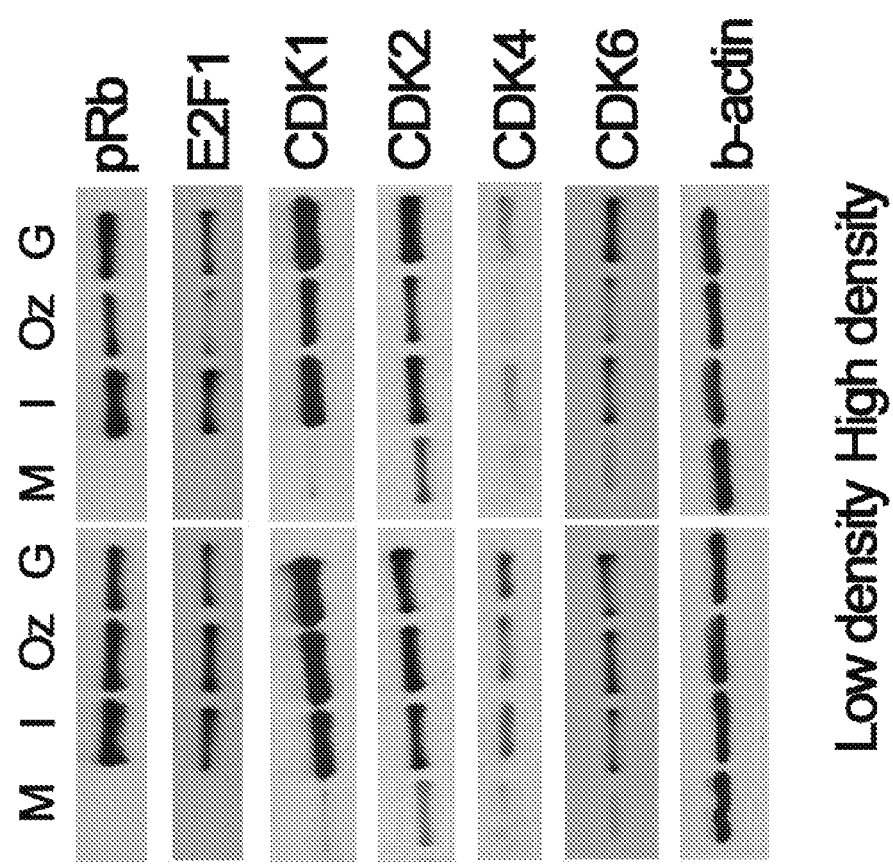

Since AS activity against HCMV was reported to be cell-density dependent (Roy S., 2015), the activity of OZ418 was tested in low density and high density human fibroblast cells. OZ418 activity was also cell-density dependent. In high-density HFFs OZ418 effectively inhibited HCMV, but in low-density HFFs its activity against HCMV was significantly reduced (FIG. 8A). The expression of pRb and CDKs was reduced in OZ418-treated HFFs in which OZ418 was CMV inhibitory, as compared to HFFs in which the drug lost its activity (FIG. 8B). Lack of HCMV inhibition by OZ418 correlated with higher levels of phosphorylated pRb and CDKs. These changes were induced by HCMV infection, since in contact-inhibited non-infected HFFs, OZ418 did not decrease the expression of pRb or any of the tested CDKs (FIGS. 6C & D). GCV did not exhibit any effects on pRb/CDKs expression confirming the specificity of the profile of cell cycle proteins to OZ418 as well as other artemisinins.

Embodiments of the disclosure concern methods and/or compositions for treating and/or preventing a CMV directly or indirectly. In certain embodiments, individuals with a CMV infection are treated with an ozonide of the present invention that inhibits CMV replication, such as OZ418, OZ439, OZ721, or a combination thereof, for example.

In certain embodiments, the level to which an ozonide of the present invention inhibits CMV replication may be any level so long as it provides amelioration of at least one symptom of the infection. The level of CMV replication by be decreased by at least 2, 3, 4, 5, 10, 25, 50, 100, 1000, or more fold compared to the level of CMV in a standard (or reference subject who has a CMV infection but has not been administered an ozonide of the present invention, in at least some cases. An individual may identify CMV replication levels of using standard methods in the art, such as northern assays or quantitative PCR, for example.

An individual known to have a CMV infection, suspected of having a CMV infection, or at risk for having a CMV infection may be provided an effective amount of an inhibitor of CMV replication, including an ozonide of the present invention such as OZ418, for example. Those at risk for PD may be those individuals having one or more genetic factors, may be of advancing age, and/or may have a family history, for example.

In particular embodiments of the disclosure, an individual is given an agent for CMV in addition to the one or more ozonides of the present invention. When combination therapy is employed with one or more ozonides of the present invention, the additional therapy may be given prior to, at the same time as, and/or subsequent to the one or more ozonides of the present invention.

Pharmaceutical Preparations

Pharmaceutical compositions of the present invention comprise an effective amount of one or more of the ozonides of the present invention such as OZ418, OZ439, OZ721, or OZ513b, for example, dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that comprises at least one ozonide or additional active ingredient will be known to those of skill in the art in light of the present disclosure, as exemplified by Remington: The Science and Practice of Pharmacy, 21$^{st}$ Ed. Lippincott Williams and Wilkins, 2005, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

An ozonide of the present invention may comprise different types of carriers depending on whether it is to be administered in solid, liquid or aerosol form, and whether it need to be sterile for such routes of administration as injection. The present compositions can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

One or more ozonides of the present invention may be formulated into a composition in a free base, neutral, or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present disclosure, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art. In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include one or more ozonides of the present invention, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, an ozonide of the present invention may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

Alimentary Compositions and Formulations

In one embodiment of the present disclosure, one or more ozonides are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792, 451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, cornstarch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present disclosure may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Parenteral Compositions and Formulations

In further embodiments, one or more ozonide(s) of the present invention may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneously, or intraperitoneally U.S. Pat. Nos. 6,7537,514, 6,613,308, 5,466,468, 5,543,158; 5,641,515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in isotonic NaCl solution and either added hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

Miscellaneous Pharmaceutical Compositions and Formulations

In other preferred embodiments of the invention, the active compound (one or more ozonide(s) of the present invention) may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

METHODS/EXAMPLES

The following Methods/Examples have been included to provide guidance to one of ordinary skill in the art for practicing representative embodiments of the presently disclosed subject matter. In light of the present disclosure and the general level of skill in the art, those of skill can appreciate that the following Methods/Examples are intended to be exemplary only and that numerous changes, modifications, and alterations can be employed without departing from the scope of the presently disclosed subject matter. The following Methods/Examples are offered by way of illustration and not by way of limitation.

Materials and Methods

Compounds: The synthesis of 1,2,4-trioxalanes has been described. AS and ganciclovir (GCV) were obtained from Sigma-Chemicals (St. Louis, MO). The compounds were dissolved in dimethyl sulfoxide (DMSO) and stocks of 10 mM were stored at −80° C. The concentration of each compound was calculated and adjusted by volume such that it was constant throughout the experiment.

Viruses: The pp28-luciferase Towne CMV strain was constructed as previously described (31). The recombinant virus expresses luciferase under the control of UL99 (pp28) late promoter 48-72 h post infection (hpi). Luciferase expression from this promoter is almost completely inhibited in the presence of viral DNA polymerase inhibitors such as GCV and foscamet. Luciferase activity highly correlates with plaque reduction assay. The Towne CMV (ATCC VR-977) and TB40 strains (ATCC VR-1578) were used for plaque reduction, DNA replication, and cell cycle assays.

Cell Culture. Virus Infection and Anti-viral assays: HFFs passage 12-16 (ATCC, CRL-2088) were grown in Dulbecco's Modified Eagle Medium (DMEM) containing 10% fetal bovine serum (FBS) (Gibco, Carlsbad, CA) in a 5% $CO_2$ incubator at 37° C. and used for infection with pp28-luciferase Towne CMV. HCT116 (Human Colorectal Carcinoma) (ATCC, CCL-247) cells were maintained in DMEM containing 10% fetal bovine serum.

A plaque reduction assay was performed in HFFs. One day prior to infection, HFFs were seeded at $3\times10^6$ cells/24-well plate. The Towne CMV strain was diluted in DMEM to a desired titer which gave approximately 50 plaques/well and added to each well in quadruplicates. Plates were incubated for 90 minutes with shaking every 10 min; thereafter compounds were added and replenished every 3 days. After a 10-day incubation, cells were stained with crystal violet and plaques were counted at 40× magnification.

To determine the effect of cell density/cycling on the anti-HCMV activity of ozonides, HFFs were plated at $0.5\times10^6$, $1\times10^6$, $2\times10^6$ or $3\times10^6$ cells/96 well-plate 24 h prior to infection. Infection was carried out at multiplicity of infection of 1 PFU/cell (MOI=1). Following 90 minute adsorption, media containing virus was removed and replaced by DMEM with 4% FBS (Gibco) containing anti-viral compounds. Infected treated HFFs were collected at 72 hpi and pp28 activity was quantified by a Luciferase Assay Kit (Promega, Madison, WI) on GloMaxH-Multi+ Detection System (Promega) according to manufacturer's instructions. Add-on and removal experiments: HFFs were infected with the pp28-luciferase HCMV as described above. At 0, 6, 12, 24, 36 and 48 hpi, the media were replaced by the media containing OZ418 or GCV. For time-of-removal studies, media containing the compounds were removed at 0, 6, 12, 24, 36 and 48 hpi, cells were then washed three times with PBS, and drug-free medium was added. The cells were incubated at 37° C., and luciferase assays were carried out at 72 hpi.

Cell viability: Cells were seeded in 96-well plates, treated with various concentrations of ozonides and incubated at 37° C. for 3 days. Cell viability was determined by an MTT-based colorimetric assay (Sigma-Aldrich), and performed at the same time points as the antiviral assay.

Inhibition of mouse CMV replication: For infection experiments BALB/c mice, 4-6 week old, were purchased from Harlan Laboratories (Indianapolis, Ind.). The Animal Care and Use Committee of Johns Hopkins University approved the experimental procedures. After 2-3 days of adaptation to the housing environment, mice were randomly divided into several groups as follows: control, infected, infected+OZ418 1 mg/kg, 3 mg/kg or 10 mg/kg orally once daily, infected+AS 10 mg/kg orally twice daily, infected+GCV 10 mg/kg intraperitoneally twice daily. Mice were infected intraperitoneally with $10^6$ PFU/mice (0.1 mL in 0.8% saline) and all treatments were started at 24 hpi. Control mice received 0.1 ml of saline intraperitoneally. Control and infected mice received equivalent volumes of saline. Mice were sacrificed at day 14 after infection. Salivary glands, liver and spleen were harvested and stored at −80° C. Organs were homogenized in DMEM with 4% FBS at a final concentration of 100 mg/mL. Two million MEFs were seeded into 24-well plates. From each sample, 5% of the salivary gland homogenate or 10% of the liver homogenate was used for infection of MEFs in triplicates. Plaques were counted after three days.

Flow cytometry: To identify the cell cycle stage affected by OZ418, non-infected HFFs were serum starved for 72 h and then released in DMEM with 0% FBS (control for $G_0$ arrest), 10% FBS (control for cell cycle progression), or 10% FBS plus OZ418 (30 μM), AS (30 μM), or GCV (30 μM) for 24 h and 72 h, respectively. To determine the effects of OZ418 on cell cycle progression in infected HFFs, $1.0 \times 10^6$ cells were serum starved for 72 h, and then infected with HCMV Towne strain (MOI=1) followed by treatment with OZ418 (30 μM), AS (30 μM), or GCV (5 μM) for 24 h and 72 h, respectively. The cells were collected by treatment with trypsin and then washed with PBS. The collected cells were fixed in 5 ml of cold 70% ethanol overnight at 4° C. and resuspended in 500 ml of staining buffer (50 μg/ml propidium iodide [Sigma-Aldrich] and 0.2 mg/ml RNase A in PBS) for 45 min at 37° C. in 5% $CO_2$. The samples were analyzed on an LSR II flow cytometer (BD Biosciences, San Jose, CA), and at least 10,000 cells were counted for each sample. Data analysis was performed using FlowJo software (Tree Star, USA). The percentage of cells in G1/S/G2-M is shown in each condition.

SDS-PAGE and immunoblot analysis: Cell lysates were quantified for total protein content using Pierce bicinchoninic acid (BCA) protein assay kit (Thermo-Fisher Scientific, Waltham, MA). Equivalent amounts of protein were mixed with an equal volume of sample buffer (125 mM Tris-HCl [pH 6.8], 4% SDS, 20% glycerol, 5% β-mercaptoethanol) and boiled at 100° C. for 10 min. Denatured proteins were resolved in Tris-glycine polyacrylamide gels (10% to 12%) and transferred to polyvinylidene difluoride membranes (Bio-Rad Laboratories, Hercules, CA) by electroblotting. Membranes were incubated in blocking solution (5% nonfat dry milk/BSA and 0.1% Tween 20 in PBS [PBST]) for 1 h, washed three times with PBST, and incubated primary antibodies diluted in 5% milk or BSA (for pRb) at 4° C. overnight. The membranes were washed with PBST, followed by incubation with horseradish peroxidase (HRP)-conjugated secondary antibodies in 5% milk/BSA for 1 h at room temperature. After three washing steps with PBST, protein bands were visualized by chemiluminescence using SuperSignal West Pico reagent (Pierce Chemical, Rockford, IL). The following antibodies were used: mouse monoclonal anti-pp65 antibody (Vector Laboratories, Burlingame, CA), mouse anti-IE1 and IE2 monoclonal antibody (MAb810, EMD Millipore Corporation, Temecula, CA); mouse anti-UL44 monoclonal antibody (Santa Cruz Biotechnology, Santa Cruz, CA); rabbit anti-phospho polyclonal Rb antibody (Ser 807/811) (Cell Signaling Technology, Beverly, MA), rabbit anti-CDK1, 2, 4, 6 polyclonal antibodies (Santa Cruz Biotechnology), mouse anti-β-actin monoclonal antibody (Santa Cruz Biotechnology). HRP-conjugated goat anti-rabbit IgG antibody (Cell Signaling Technology, Beverly, MA), and HRP-conjugated sheep anti-mouse IgG (GE Healthcare, Waukesha, WI).

Drug combination and analysis: Drug combinations were performed as previously reported (33). Briefly, $2 \times 10^6$ HFFs were seeded in a 96-well plate and infected with the pp28-luciferase Towne CMV strain at MOI=1. First, a dose response curve was generated for each drug individually to determine its $EC_{50}$. Then, drugs were combined at twice their $EC_{50}$, diluted in DMEM with 4% FBS, followed by serial dilution and added together after infection. Luciferase activity of the combination and each drug individually was quantified at 72 hpi. The Bliss model was used to calculate the effect of each drug combination on pp28-luciferase activity. In this model, drug combination represents the product of two probabilistically independent events as described in the following equation (23):

$$F_{U1+2} = F_{U1} \cdot F_{U2} = \frac{1}{1+\left(\frac{D_1}{EC_{50(1)}}\right)^{m_1}} \cdot \frac{1}{1+\left(\frac{D_2}{EC_{50(2)}}\right)^{m_2}}$$

Where D is the drug concentration, m is the slope, and $EC_{50}$ is the effective concentration resulting in 50% virus inhibition. The combined effect of two inhibitors ($F_U$, fractional unaffected) is computed as the product of individual effects of the two inhibitors, $F_{U1}$ and $F_{U2}$. If the ratio of observed fold inhibition divided by the expected fold inhibition is greater than 1, the compounds are synergistic. If the ratio is less than 1, the combination is considered antagonistic, and if it equals to 1 the combination is additive.

Statistical analysis: A student t-test was performed using Sigmaplot (Systat Software, San Jose, CA) and Graphpad Prism (Graphpad Software, La Jolla, CA). P values of <0.05 were considered significant.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of inhibiting herpesvirus replication comprising the following steps:
   providing a biological sample comprising a virus that is replicating;
   applying a compound of Formula I to the sample;

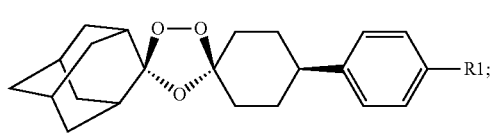
(I)

wherein R1 is selected from the group comprising alkyl, cycloalkyl, ether, carboxylic acid, weak base, or other polar functional groups or a pharmaceutically acceptable salt, solvate, or stereoisomer thereof; and inhibiting the replication of the virus.

2. The method of claim 1, wherein the herpesvirus is selected from the group comprising a cytomegalovirus (CMV), a varicella zoster (VZV), a herpesvirus 1 (HSV1), a herpesvirus 2 (HSV2), a human herpesvirus 6 (HHV6), a human herpesvirus 8 (HHV8) or a combination thereof.

3. The method of claim 1, wherein the compound of Formula I, salt, solvate, or stereoisomer thereof is one of the following:

OZ418
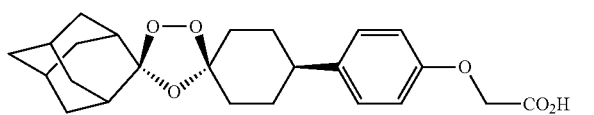

OZ439
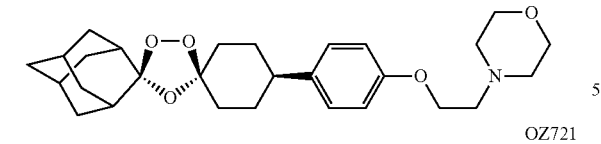

OZ721
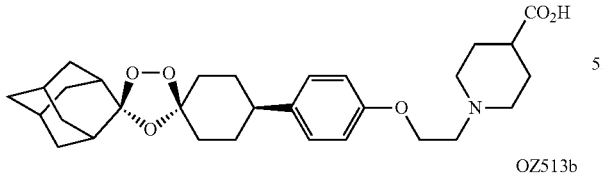

OZ513b
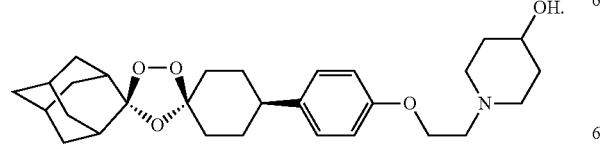

4. The method of claim 1, wherein the biological sample is selected from the group consisting of blood, cells, tissue, or a combination thereof.

5. The method of claim 1, wherein the virus is a cytomegalovirus (CMV).

6. The method of claim 1, wherein the compound of Formula I, salt, solvate, or stereoisomer thereof is

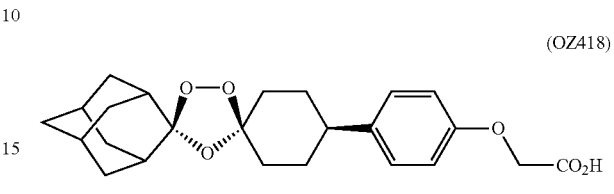
(OZ418)

or

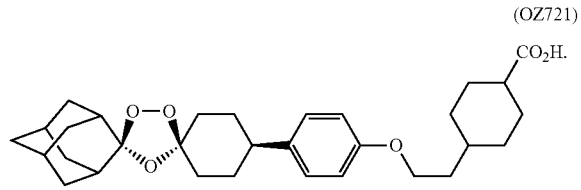
(OZ721)

7. The method of claim 6, further comprising co-applying ganciclovir to the sample.

8. A method of treating a herpesvirus infection in a subject in need thereof comprising:
   administering to the subject an effective amount of a compound of Formula I

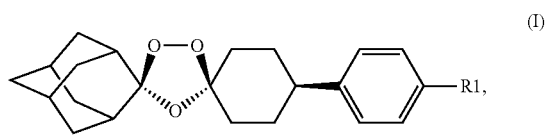
(I)

or a pharmaceutically acceptable salt, solvate, or stereoisomer thereof, wherein R1 is selected from the group comprising alkyl, cycloalkyl, ether, carboxylic acid, weak base, or other polar functional groups.

9. The method of claim 8, wherein the compound of Formula I, salt, solvate or stereoisomer thereof is one of the following:

OZ418
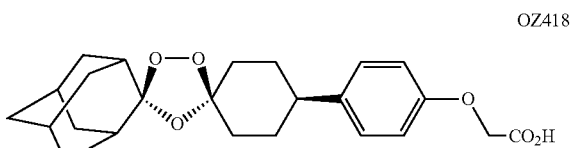

OZ439
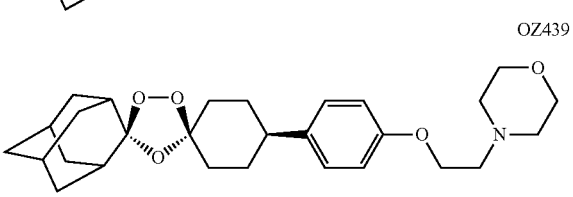

-continued

OZ721

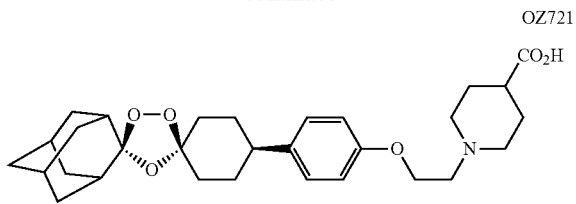

OZ513b

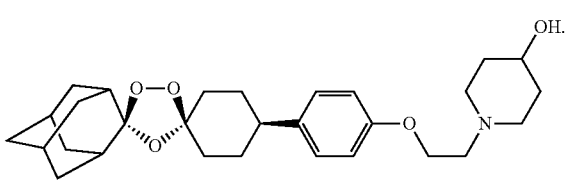

10. The method of claim 8, wherein the herpesvirus is selected from the group comprising a cytomegalovirus (CMV), a varicella zoster (VZV), a herpesvirus 1 (HSV1), a herpesvirus 2 (HSV2), a human herpesvirus 6 (HHV6), a human herpesvirus 8 (HHV8) or a combination thereof.

11. The method of claim 8, wherein the virus is a cytomegalovirus (CMV).

12. The method of claim 8, wherein the compound of Formula I is administered to the subject in a pharmaceutical composition comprising a pharmaceutically acceptable carrier.

13. The method of claim 12, wherein the pharmaceutical composition of the compound of Formula I is administered to the subject topically.

14. The method of claim 12, wherein the pharmaceutical composition of the compound of Formula I is administered to the subject orally.

15. The method of claim 8, wherein the compound of Formula I, salt, solvate, or stereoisomer thereof is (OZ418)

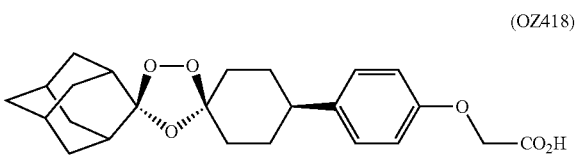

or (OZ721)

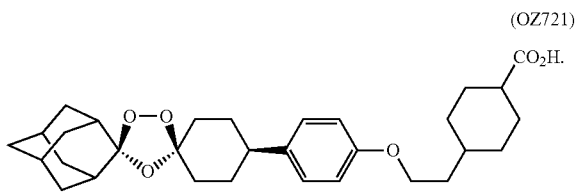

16. The method of claim 15, further comprising co-administering ganciclovir to the subject.

* * * * *